United States Patent [19]

Kim

[11] 3,964,982

[45] June 22, 1976

[54] METHOD AND APPARATUS FOR CONTROLLING THE DEGREE OF HYDRATION IN SEALING OF ANODIZED ALUMINUM

[75] Inventor: Duk Hwang Kim, Bellevue, Wash.

[73] Assignee: The Boeing Company, Seattle, Wash.

[22] Filed: June 16, 1975

[21] Appl. No.: 587,177

Related U.S. Application Data

[63] Continuation-in-part of Ser. No. 490,832, July 22, 1974, abandoned.

[52] U.S. Cl. .................................. 204/1 T; 73/73; 204/35 N; 324/71 R; 427/8; 427/331
[51] Int. Cl.² ...................... G01N 27/26; C25D 5/44
[58] Field of Search ............... 204/1 T, 35 N; 73/73; 324/71 R; 148/6.27; 427/8, 331

[56] References Cited
UNITED STATES PATENTS

| | | | |
|---|---|---|---|
| 2,894,882 | 7/1959 | Strodtz | 204/1 I |
| 3,293,155 | 12/1966 | Stone | 204/1 |
| 3,356,597 | 12/1967 | Schmidt | 204/1 T |
| 3,364,554 | 1/1968 | Lindblad | 204/1 T |
| 3,384,556 | 5/1968 | Rohde | 204/1 T |
| 3,419,479 | 12/1968 | Klein | 204/1 T |
| 3,649,472 | 3/1972 | Morrissey et al. | 204/1 T |

OTHER PUBLICATIONS

S. Wernick, "Surface Treatment & Finishing of Light Metals," *Metal Finishing*, Aug., 1956.
R. C. Spooner et al., "X-Ray Emission Spectroscopic Study of the Sealing of $H_2SO_4$ Anodic Films on Aluminum", *Plating*, Apr. 1968.
G. A. Dorsey, "Effect of Sealing Variables on the Degree-of-Seal", *J. Electrochem. Soc.*, Oct., 1970.
R. C. Spooner, "Sealing of Anodic Films on Aluminum & Its Alloys", *Metal Finishing*, Dec. 1968-Jan. 1969.

*Primary Examiner*—T. Tung
*Assistant Examiner*—Aaron Weisstuch
*Attorney, Agent, or Firm*—Morris A. Case; Bernard A. Donahue

[57] ABSTRACT

A mixed potential measurement utilizing a strip chart recording voltmeter coupled between the metal and its oxide immersed in the sealing solution is determinative of percent hydration of the part in situ during the sealing process.

2 Claims, 5 Drawing Figures

EFFECT OF SEALING TEMPERATURE ON MIXED POTENTIAL

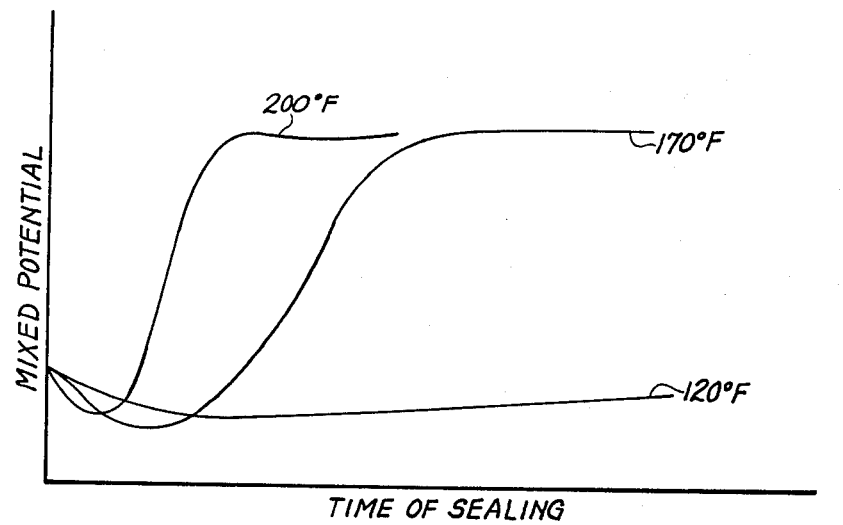
Fig. 1 — EFFECT OF SEALING TEMPERATURE ON MIXED POTENTIAL
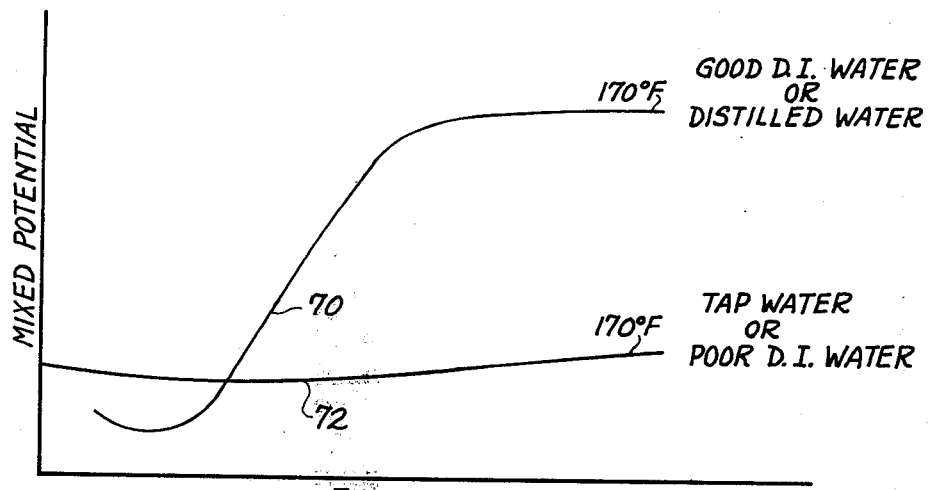
Fig. 2 — EFFECT OF SEALING WATER ON MIXED POTENTIAL
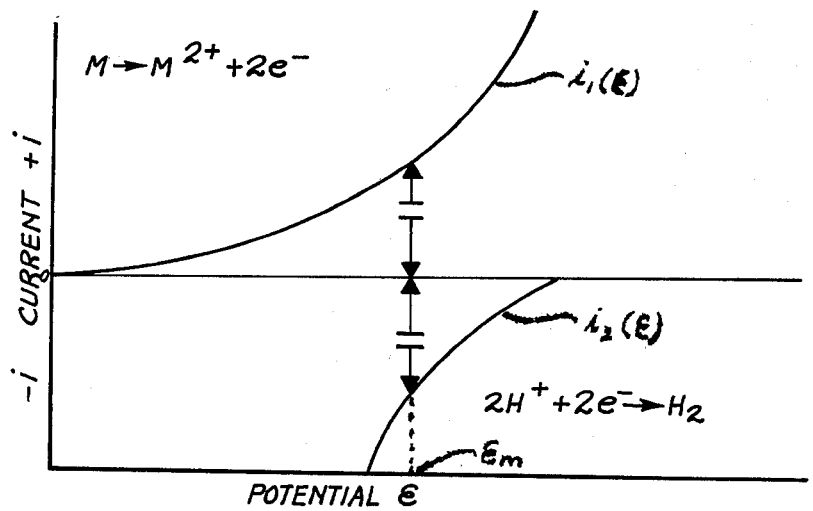
Fig. 3

METHOD AND APPARATUS FOR CONTROLLING THE DEGREE OF HYDRATION IN SEALING OF ANODIZED ALUMINUM

This is a continuation-in-part of copending parent application, Ser. No. 490,832, filed July 22, 1974, now abandoned, and claims priority to the common subject matter of that application.

It has long been known that anodized aluminum surfaces must be sealed to inhibit corrosion of the aluminum when in use. The means for sealing the porous surface created by anodizing is to immerse the newly anodized part in hot water for a span of time. The water combines with the generated porous oxide and seals it off to prevent corrosion of the aluminum. One means of determining when the part has been sufficiently sealed is to determine the weight percent of hydration by gravimetric control. Painted aluminum parts must be sealed sufficiently to prevent corrosion and also provide a surface to which the paint will uniformly adhere. It is known that undersealing will provide an excellent surface for paint, but will allow corrosion of the aluminum; and that sufficient or oversealing will prevent corrosion, but oversealing may cause crazing of a painted surface. Thus, the weight percent of hydration is determined at which the sealed aluminum part will be both corrosion resistant and free from crazing when painted.

This invention relates to a method for controlling the percent weight hydration during aluminum anodize sealing and more particularly it relates to the determination of mixed potential of metal parts during anodize sealing, which mixed potential measurement is a function of percent hydration.

A problem has existed in industry of controlling the degree of hydration in the sealing of anodized aluminum. The proper degree of hydration must be obtained so the coating will meet the divergent requirements of both corrosion resistance and paint adhesion. Part of the problem is with the inherent inaccuracy of the presently utilized gravimetric control method. Also presently, percent hydration is determined gravimetrically using test specimens.

It is accordingly an object of the present invention to provide a direct in situ method for determining percent hydration to avoid high rejection rates, unreliability, and the time consumption which results from test specimen utilization by the gravimetrical process.

The method of measuring the potential between a substrate aluminum and its oxide coating for the purpose of determining the corrosion resistance has been known since around 1920 and is based on a mixed potential concept whereas the present method relates to utilization of the mixed potential concept in determining the degree of anodized aluminum sealing.

U.S. Pat. No. 3,293,155 to Stone relates to a method of evaluating the corrosion resistance of a coating by applying a voltage across the coating for a fixed time period. The present method does not apply a voltage across the coating.

U.S. Pat. No. 3,649,472 to Morrissey et al, relates to the porosity of an electroplated specimen, measured as apparent area fraction of the anode, specifically, measurement of porosity of gold electroplates on copper by corrosion potentials.

The preferred embodiment of the present invention measures and records mixed potential utilizing a platinized platinum electrode immersed in the sealing bath, coupled to one terminal of the recording voltmeter with the second terminal of the recording voltmeter coupled to the bare metal of the anodized part. Mixed potential readings representative of percent hydration result in sealing process control of less than about 10 minutes whereas the gravimetric method using a test specimen requires about 10 hours flow time.

Further advantages of the sealing process control will become apparent from a reading of the subsequent specification and drawings that include:
1. capability of in situ process control;
2. simplicity of operation; and
3. low cost of operation.

Other objects and advantages of this invention will be made more apparent as this description proceeds, particularly when considered in connection with the accompanying drawings in which:

FIG. 1 is a graph showing qualitatively the effect of sealing temperature on mixed potential;

FIG. 2 is a graph showing the effect of sealing water conditions on mixed potential;

FIG. 3 is a graph showing the formation of mixed potential $\epsilon_m$;

Figure 4:
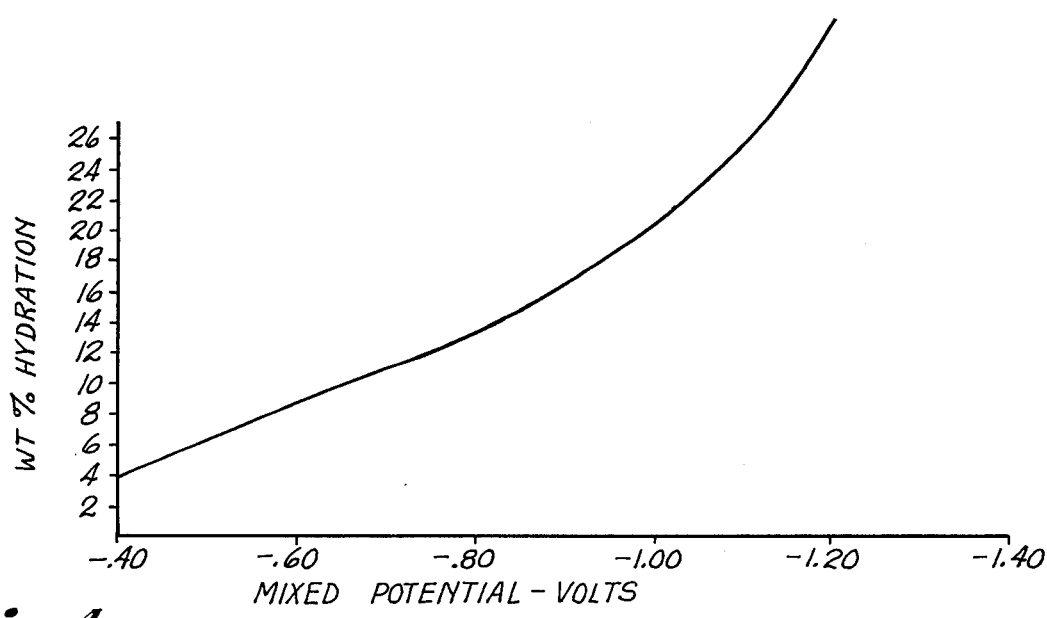
FIG. 4 is a graph showing the correlation between percent hydration and mixed potential.
Figure 5:
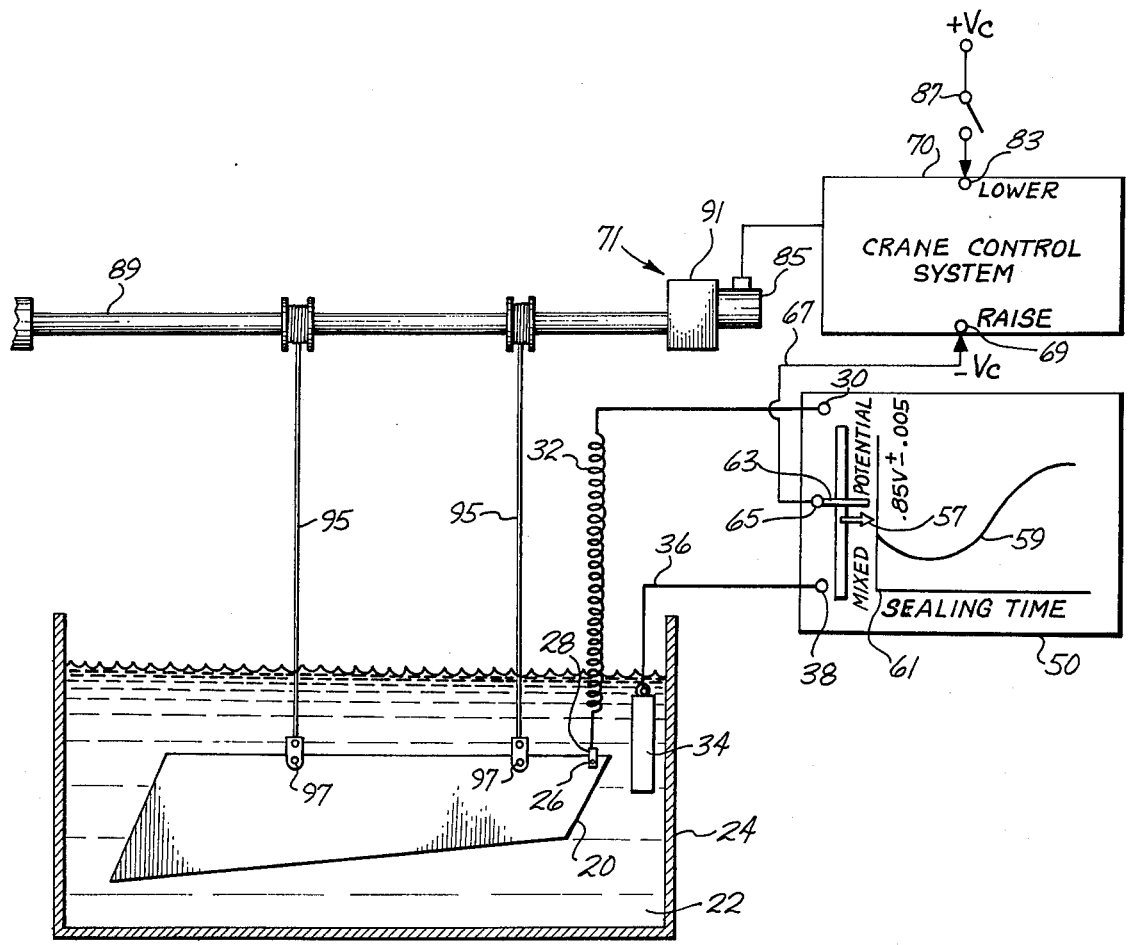
FIG. 5 is illustrative of an apparatus according to an embodiment of the invention for controlling the percent hydration of parts immersed in a sealing solution.

While the aluminum anodize sealing process is shown automatically controlled by mixed potential measurement to remove parts as shown in the system of FIG. 5, an introductory understanding of the present mixed potential method for monitoring the degree of sealing (percent hydration) is essential to a more complete understanding of the present invention and will now be explained in the following description and FIGS. 1 to 4. In monitoring the degree of sealing, the mixed potential may be considered as the open potential between a metal and and its oxide, and is changed as the sealing reaction progresses as will be seen in detail hereinafter.

Mixed potentials are hereinafter measured in accordance with the invention in the apparatus of FIG. 5 at open circuit when the metal part is immersed in a sealing solution. The potential at open circuit is determined by the kinetics of the two coupled electrode processes and the algebraic sum of the current-potential curves for each process.

The behavior of a base metal electrode having an anodic reaction described as $M \rightarrow M^{2+} + 2e^-$ on which a simultaneous cathodic reaction $2H^+ + 2e^- \rightarrow H_2$ occurs is illustrated in FIG. 3 where E is potential, $i_1(\epsilon)$ is the polarization (E–i) curve for the anodic reaction, and $i_2(\epsilon)$ is the polarization curve for the cathodic reaction. The potential $\epsilon$ at which there is a net zero current ($i_1(\epsilon) + i_2(\epsilon) = 0$; i.e., the current due to anodic reaction is equal to the current due to cathodic reaction) is neither the equilibrium potential of the anodic process nor the equilibrium potential of the reduction process, but is the so-called mixed potential $\epsilon m$ of the metal. The value of the mixed potential depends essentially upon the individual polarization curves ($i_1(\epsilon)$ and $i_2(\epsilon)$) which are greatly dependent upon the properties of the metal surface and the environment, while the equilibrium potentials are not.

An anodized aluminum panel 20 (See FIG. 5) was immersed in a sealing bath comprising a sealing solution 22 of deionized water in an open top tank 24. An electrical contact 26 with the bare metallic aluminum surface of anodized part 20 was made utilizing a metal clamp 28 which was insulated except at contact point 26. A pinpoint contact area is satisfactory in this regard. Clamp 28 was coupled to a first input terminal 30 of recording voltmeter 50 by means of a conductor comprising wire 32. A reference electrode comprising platinized platinum electrode 34 was immersed in sealing bath 22 and coupled by means of wire 36 to the second input terminal 38 of recording voltmeter 50. Strip chart recording voltmeter 50 was adjusted to measure across input terminals 38 and 30, voltages from 0 to −2.0 volts with a chart speed of 1 inch per minute.

While reference electrode 34 has been referred to hereinbefore as a platinized platinum electrode, and such reference electrode per se is known, it is of importance as utilized in the present system in providing more accurate information over longer periods of time in usage than simply a platinum electrode and consequently its preparation and special merits will now be described.

Platinum is an excellent reference electrode because of its large exchange current and its chemical resistance. Platinizing increases the performance of a platinum electrode by increasing its active surface. The platinized platinum electrode is very versatile since it can be directly introduced in most solutions without difficulty, it indicates the reversible hydrogen potential of acid solutions, and it can be used as a means of determining when oxygen has been completely purged from electrolytes. Also, it serves as an excellent auxiliary electrode because of its very low polarization in most solutions. A platinized platinum electrode can be readily assembled. The most convenient method is to use solid platinum rod which is drilled and tapped, and mounted with a Teflon gasket.

After mounting the platinum electrode, it is cleaned in hot, aqua regia (1 part concentrated nitric acid and 3 parts concentrated hydrochloric acid) until any black, porous platinum deposit is removed. Following this operation, which is performed in a hood, electrodes are washed in doubly distilled water and dried. Platinizing is achieved by electrolyzing in a solution containing 3 percent platinic chloride, and 0.02 percent lead acetate. Lead acetate serves to produce a smooth, porous deposit of platinum. It is convenient to platinize two electrodes simultaneously. The two electrodes are connected to a battery or variable voltage D.C. power supply and a current of 40 ma./cm$^2$ is passed through them. Electrolysis is continued for a total of 4 minutes and current is reversed at the end of each minute by changing polarity. At the end of this operation, the electrodes should be covered with a black velvety deposit of platinized platinum. Electrodes are then cleaned to remove occluded chlorine by electrolyzing at a current density of 50–100 ma/cm$^2$ in 10 percent sulfuric acid for 4 minutes with current reversal at the end of each minute. The electrodes are carefully rinsed in doubly distilled water, and stored in a test tube containing distilled water to prevent atmospheric dust contamination. The platinized platinum electrodes should never be allowed to dry. Also, they should never be touched with the fingers since the coating is very soft and can be readily transferred to other electrodes and cause contamination.

Platinized platinum is very versatile; it can be used in almost any solution over a wide range of temperatures without special precautions. Further, it can be used as an auxiliary electrode to supply current in a polarization cell, and after waiting for a sufficient period, it will return to its original steady-state condition. Hence, appreciable currents can be passed through a platinized platinum electrode without affecting its accuracy.

A platinized platinum electrode may be conveniently calibrated by measuring its potential in hydrogen saturated, normal sulfuric acid at room temperature. Its potential should be −0.263 ±0.002 volt SCE. A platinized platinum electrode has a limited life. With passing time, its approach to equilibrium or steady state potentials becomes slower as a result of contamination by airborne dust and trace impurities present in all solutions. If an electrode requires extensive time to reach steady state potential (the usual time for a platinum electrode to achieve reversible hydrogen potential in a hydrogen saturated solution is 1 to 2 minutes or less), the electrode should be cleaned and replatinized.

As previously noted there is a direct correlation between weight percent hydration of an anodized part and sealing of the oxide surface of the part. The correct range of sealing to satisfy both corrosion resistance and paint adhesion may thus be determined from weight percent hydration. The relationship of weight percent hydration versus the mixed potential makes it possible to directly control the amount of sealing by use of the mixed potential method. FIG. 4 shows the relationship between mixed potential and weight percent hydration. FIG. 4 is a composite of a series of tests performed on test coupons. The coupons were anodized, then sealed in deionized water at varying times determined by mixed potentials.

The coupons were then tested in sets sealed to provide the same mixed potential at the termination of sealing. Different coupons in each set were tested to determine weight percent hydration with gravimetric methods, corrosion resistance in salt spray chamber, and for resistance to crazing of painted surfaces. The relation of weight percent hydration versus mixed potential is shown in FIG. 4. Tests showed the aluminum surfaces sealed to a weight percent hydration of from about 13 to 17 which corresponds to a mixed potential of about minus 0.80 to minus 0.90 gives an effective sealing for both corrosion resistance and resistance to crazing of the painted surface. When part 20 comprising an anodized panel is immersed in sealing bath 22 and as hereinafter discussed, the apparatus of FIG. 5 automatically removes part 20 from bath 22 when a predetermined mixed potential voltage is reached determinative of proper percent hydration to give the desired amount of sealing of the part.

FIG. 1 shows qualitatively the effect of sealing temperature of sealing bath 22 on achieving the desired mixed potential voltage on a time scale for immersion of part 20. It can thus be seen that temperature of sealing bath 22 (e.g. too low) can prevent the achievement of desired percent hydration (mixed potential voltage level) within a given bath time or even not at all. FIG. 2 is a graph of mixed potential voltage versus time of sealing for deionized water (Curve 70) and tap water or poorly deionized water (Curve 72). It can be seen from FIG. 2 that failure to reach the desired mixed potential voltage (percent hydration) also within a given sealing bath time period can also be indicative of poor bath quality so that the operator can immediately take proper action during the sealing process to properly seal the part under proper bath conditions without loss of time, or continue with a resultant unsatisfactory sealed part as a result. The present method and apparatus for also determining whether the sealing solution is adequate (to provide proper sealing within the normal time period, less than 10 minutes) is also deemed a significant contribution in time savings in processing of parts in the case where the sealing bath conditions have become unsatisfactory.

Returning now to further description of the apparatus of FIG. 5 in which it was earlier noted that the mixed potential voltage was developed between contact point 26 and reference electrode 34 and applied through coupling means 32 and 36 to the input terminals 30 and 38 of strip chart recording type voltmeter 50, it will be further noted that when a preset voltage level (set by adjustable set contact pointer 63) is reached (here 0.85 volts negative plus or minus 0.005 volts), pointer 57 (which is tracing out a curve 59 of mixed potential versus time on strip chart 61) then makes contact with set contact pointer 63 causing a negative control voltage (of 0.85 volts plus or minus 0.005 volts) to appear at output terminal 65. This control voltage $-V_c$ is coupled through coupling means 67 comprising a connector cable to an input terminal 69 of crane control system 70 which is operative to raise anodized part 20 out of sealing bath 22. When a positive polarity control voltage $+V_c$ is applied to the other input terminal 83 of crane control system 70 by closure of switch 87 manually by the operator, reversible motor 85 is reversed to drive output shaft 89 through gear reduction unit 91 in the opposite direction to lower part 20 into the sealing bath 22. Cables 95 fastened permanently to shaft 89 and wound therearound terminate in clamps 97 which hold part 20. While a particular means 70, 85, 91, 89, 95, and 97 responsive to a first control signal ($+V_c$) for lowering part 20 into sealing bath 22 within tank 24, and responsive to a second control signal ($-V_c$) for raising part 20 out of sealing bath 22 within tank 24 is shown for purposes of illustration, any equivalent crane 71 and crane control system 70 therefore known by those skilled in the art which is responsive to first and second control signals respectively for lowering and raising part 20 could be utilized.

After immersion of part 20 subsequent to closure of switch 87 by the operator, and with pointer 63 set as hereinbefore described to the desired voltage level, the operator awaits the withdrawal of the part (for between −0.80 volts and −0.90 volts preferably −0.85 volts mentioned previously, about 15 percent weight hydration is achieved, as can be seen from the graph of FIG. 4) automatically upon the appearance of second command signal ($-V_c$) at terminal 69 of crane control system 70. In the meantime, strip chart 61 moving at 1 inch per minute is observed, and under normal conditions using good deionized sealing water (having a conductivity of higher than about 1 megaohmcentimeter measured at 25°C. which is room temperature) and having a temperature of between about 155°F. and 165°F., part 20 is withdrawn automatically in the aforementioned manner in a sealing time of less than about 10 minutes. Upon the non-occurrence of withdrawal within such time period, the strip chart is observed for a time period of 30 minutes after immersion so that upon further occurrence or non-occurrence of withdrawal due to failure to reach the mixed potential representative of desired percent weight hydration, the graph plotted in ink by pointer 57 may be observed and the plot compared with the curves of FIGS. 1 and 2 characteristic of sealing water temperature and quality, respectively, to determine how the sealing bath water must be changed to achieve the desired result with the next part within the aforementioned 10 minute period. The present apparatus and method thus also enables the operator to obtain the sealing of anodized metal parts having the desired weight hydration and maintain desired sealing solution characteristics to continuously provide the desired results in successive immersion of parts.

I claim:

1. In the process for producing a sealed, anodized film on an aluminum surface, said process including the steps of anodizing said surface so as to produce a porous aluminum oxide film on said surface and thereafter sealing said surface, in which the improvement comprises a process for evaluating the degree of hydration during said sealing step including the step of measuring the mixed potential of the anodized aluminum surface; electrically recording said mixed potential with respect to time; and then automatically terminating said sealing step when said mixed potential equals a predetermined voltage representative of the preselected degree of hydration.

2. The process for evaluating the degree of hydration during sealing of an anodized aluminum part immersed in a sealing solution, comprising the steps of: measuring and recording the mixed potential of said anodized aluminum part during said sealing, and continuing said measuring and recording of said mixed potential when said mixed potential does not exceed, in a predetermined time internal, a predetermined voltage level representative of desired hydration level in order to evaluate the quality of said sealing solution.

* * * * *